(12) United States Patent
Vanhove et al.

(10) Patent No.: US 8,785,138 B2
(45) Date of Patent: Jul. 22, 2014

(54) MONOVALENT LIGANDS OF THE HUMAN CD28 RECEPTOR

(75) Inventors: Bernard Vanhove, Reze (FR); Caroline Mary, Sainte Pazanne (FR)

(73) Assignees: Effimune, Nantes (FR); Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 13/501,015

(22) PCT Filed: Oct. 8, 2010

(86) PCT No.: PCT/IB2010/054562
§ 371 (c)(1),
(2), (4) Date: Jul. 2, 2012

(87) PCT Pub. No.: WO2011/042891
PCT Pub. Date: Apr. 14, 2011

(65) Prior Publication Data
US 2013/0058933 A1   Mar. 7, 2013

(30) Foreign Application Priority Data
Oct. 9, 2009 (FR) ...................................... 09 04866

(51) Int. Cl.
*G01N 33/53* (2006.01)

(52) U.S. Cl.
USPC .......................................................... 435/7.1

(58) Field of Classification Search
CPC ...................... C07K 16/2818; C07K 14/70521
See application file for complete search history.

(56) References Cited

U.S. PATENT DOCUMENTS

| | | | |
|---|---|---|---|
| 8,168,759 B2 * | 5/2012 | McKinnon et al. | 530/387.3 |
| 2008/0095774 A1 * | 4/2008 | O'Hara et al. | 424/135.1 |
| 2011/0097339 A1 * | 4/2011 | Holmes et al. | 424/158.1 |
| 2011/0262427 A1 * | 10/2011 | Hermans et al. | 424/130.1 |

FOREIGN PATENT DOCUMENTS

| | | |
|---|---|---|
| WO | 02/47721 | 6/2002 |
| WO | 02/051871 | 7/2002 |
| WO | 2009/018441 | 2/2009 |

OTHER PUBLICATIONS

Evans et al., Nature Immunology, 2005, 6: 271-279.*
Beyersdorf et al. (Blood, 2008, 112: 4328-4336).*
Luhder et al. (J. Exp. Med., 2003, 197: 955-966).*
Peach et al. (J. Exp. Med., 1994, 180: 2049-2058).*
Sorensen et al. (J. Immunol., 2004, 172: 6803-6809).*
Nunes, CD28 mAbs With Distinct Binding Properties Differ in Their Ability to Induce T Cell Activation: Analysis of Early and Late Activation Events, International Immunology, 5, pp. 311-315, 1992.
Vanhove, Selective Blockade of CD28 and not CTLA-4 With a Single-Chain Fv-alpha1 Antitrypsin Fusion Antibody, Blood, 102, pp. 564-570, 2003.
Tan, Induction of Alloantigen-Specific Hyporesponsiveness in Human T Lymphocytes by Blocking Interaction of CD28 With Its Natural Ligand B7/BB1, Journal of Experimental Medicine, 177, pp. 165-173, 1993.

* cited by examiner

*Primary Examiner* — Ilia Ouspenski
(74) *Attorney, Agent, or Firm* — Morgan, Lewis & Bockius LLP

(57) ABSTRACT

The invention relates to monovalent ligands of the human CD28 receptor, which can selectively block the interaction between CD28 and B7 without activating the CD28 receptor. Said ligands can be used in particular in the production of immunosuppressant drugs, selectively blocking T lymphocyte activation phenomena involving the CD28 receptor.

2 Claims, 1 Drawing Sheet

```
       A      A'        B               C                    C'       C''
NKILVKQSPMLVAYDNAVNLSCKYSYNLFSREFRASLHKGIDSAVEVCVVYGNYSQQLQVYS

D          E              F              G       G'
KTGFNCDGKLGNESVTFYLQNLYVNQTDIYFCKIEVMYPPPYLDNEKSNQTIIHVKGKHLCP

SPLFPGPSKP
```

MONOVALENT LIGANDS OF THE HUMAN CD28 RECEPTOR

RELATED APPLICATIONS

The present application is a U.S. National Phase Application of International Application No. PCT/IB2010/054562 (filed Oct. 8, 2010) which claims priority to French Application No. 0904866 (filed Oct. 9, 2009) which are hereby incorporated by reference in their entirety.

SEQUENCE LISTING SUBMISSION VIA EFS-WEB

A computer readable text file, entitled "045636-5190_SequenceListing.txt," created on or about Apr. 9, 2012, with a file size of about 3 kb contains the sequence listing for this application and is hereby incorporated by reference in its entirety.

The present invention relates to the selection of monovalent ligands of the human CD28 receptor which make it possible to block CD28/B7 interaction without activating CD28, and to the uses thereof.

T lymphocyte activation requires an activating signal, induced by the recognition, by the T receptors (TCRs), of the antigen associated with the class I or II major histocompatibility complex (MHC) and presented by the antigen-presenting cells (APCs). However, this activation leads to T cell proliferation and the secretion of immunomodulatory cytokines (such as interleukin 2, gamma-interferon or interleukin 4) only if other T cell costimulatory systems are also activated.

One of the most important systems for regulating T lymphocyte activation is the B7/CD28/CTLA4 molecular system. This system plays, for example, an essential role in transplant rejection mechanisms [Woodward et al., Transplantation, 66, 14-20, (1998)]. The B7.1 (CD80) and B7.2 (CD86) molecules, collectively denoted hereinafter under the term "B7", which are carried by the APCs, can activate the CD28 receptor and also the CTLA4 receptor of T lymphocytes. CD28 activation delivers to the T lymphocyte a positive signal which stimulates the cell; on the other hand, CTLA4 activation delivers a negative signal resulting in a non-response (anergy) [Fallarino et al, J. Exp. Med., 188, 205-210, (1998)].

Resting T lymphocytes express a large number of CD28, and very little CTLA4. During a first cognitive contact between an APC and a T lymphocyte, the CD28/B7 interaction is favored, thereby activating the cell. It is only several hours after the initiation of activation, owing to the increase in membrane expression of CTLA4, the affinity of which for B7 is to 10 times greater than that of CD28, that the B7/CD28 interaction is displaced in favor of a B7/CTLA4 interaction.

Selective inhibition of the agonist signal delivered to the T cell by CD28 while leaving intact the antagonist system made up of the CTLA4/B7 pair, by means of specific blocking of the CD28/B7 interaction, may make it possible to prevent T lymphocyte activation, and thus to promote the induction of tolerance in the case of organ transplantation and also in the case of the treatment of autoimmune diseases.

This selective inhibition can be obtained by targeting the CD28 receptor of T cells, in particular using an antibody directed against CD28.

However, not all antibodies have the same capacity to selectively inhibit the CD28/B7 interaction. Indeed, a large number of them, when they are used in their divalent native form, bring about dimerization of CD28, which causes its activation, and if they are used in the form of monovalent fragments, which do not bring about dimerization of CD28, they no longer have an inhibitory effect of the CD28/B7 interaction. Other anti-CD28 antibodies, called superagonist antibodies, are capable of activating T lymphocytes, even in the absence of the activation signals induced by the TCR/MHC interaction. These various properties of anti-CD28 antibodies have been attributed to their ability to recognize various regions of CD28 (Int. Immunol., 5, 311-315, 1993; Luhder et al., J Exp Med 197, 955-66 2003).

During previous studies, the team of inventors selected, from among anti-CD28 monoclonal antibodies described by Nunes et al. (1993, mentioned above), an antibody called CD28.3, the monovalent fragments of which have the ability to inhibit the CD28/B7 interaction. The hybridoma producing the CD28.3 antibody was deposited with the CNCM [French national collection of microorganism cultures] under number 1-2582, and is described in PCT application WO 02/051871.

The inventors have now characterized the epitope recognized by the CD28.3 antibody, thereby making it possible to identify other monovalent ligands of CD28 which have the same properties as the monovalent fragments derived from CD28.3. This epitope is a conformational epitope located in domains C, D, E, F of the CD28 molecule.

The sequence of a portion of the human CD28 receptor, containing the epitope recognized by the CD28.3 antibody, is represented in FIG. 1. The various domains A, A' B, C, C', C", E, F, G and G', as defined by Evans et al. (Nat Immunol., 6 (3):271-9, 2005) are indicated above the sequence. The regions constituting the epitope are highlighted in grey. This sequence is also represented in the appended sequence listing under the identifier SEQ ID NO: 1.

Consequently, the subject of the present invention is a monovalent ligand of the human CD28 receptor capable of selectively blocking the CD28/B7 interaction without activating the CD28 receptor, characterized in that it recognizes an epitope formed by the portions of the sequence SEQ ID NO: 1 which have the following sequences:

```
SREFRASLHKGL;              (SEQ ID NO: 2)

NCDGKL;                    (SEQ ID NO: 3)

VTFYLQNLYVNQTDIYFCKIEVM,   (SEQ ID NO: 4)
``` with the exception of a monovalent ligand having the CDRs of the heavy chain and the CDRs of the light chain of the CD28.3 immunoglobulin.

A "monovalent ligand" is defined herein as any ligand of the human CD28 receptor which has a single site for binding to said CD28 receptor. Said ligand is preferably a protein; it may, for example, be a monovalent fragment of an anti-CD28 antibody, or else an anticalin (Skerra et al., FEBS J., 275 (11),:2677-83, 2008).

According to one preferred embodiment of the present invention, said monovalent ligand is a protein comprising the CDRs of the heavy chain and the CDRs of the light chain of an anti-CD28 antibody which recognizes the epitope defined above. It may in particular be a monovalent fragment (Fv, Fab or scFv) of said antibody, or a recombinant protein combining said monovalent fragment with a heterologous polypeptide, as described, for example, in PCT application WO 02/051871 for the monovalent fragments of the CD28.3 antibody.

The subject of the present invention is also a method for obtaining a monovalent ligand of the human CD28 receptor capable of selectively blocking the CD28/B7 interaction without activating the CD28 receptor, characterized in that it comprises bringing monovalent ligands of the human CD28 receptor into contact with a polypeptide which has the sequence of the human CD28 receptor or a fragment thereof comprising the sequences SEQ ID NO: 2, SEQ ID NO: 3 and SEQ ID NO: 4, and selecting the ligands which recognize an epitope formed by said sequences SEQ ID NO: 2, SEQ ID NO: 3 and SEQ ID NO: 4.

The subject of the present invention is also any nucleic acid molecule encoding a monovalent ligand of the human CD28 receptor in accordance with the invention, and also any recombinant vector, in particular any expression vector, comprising said nucleic acid molecule, and any host cell transformed with said recombinant vector.

Nucleic acid molecules in accordance with the invention may advantageously comprise, in addition to a sequence encoding a protein in accordance with the invention, a sequence encoding a signal peptide allowing the secretion of said protein; they may also comprise one or more sequence(s) encoding one or more marker peptide(s) allowing the detection and/or facilitating the purification of said protein.

Expression vectors in accordance with the invention comprise at least one nucleic acid sequence encoding a protein in accordance with the invention, combined with transcription- and translation-controlling elements which are active in the host cell selected. Vectors that can be used for constructing expression vectors in accordance with the invention are known in themselves, and will be chosen in particular according to the host cell that it is desired to use.

Host cells that can be used in the context of the present invention may be prokaryotic or eukaryotic cells. Among the eukaryotic cells that can be used, mention will in particular be made of plant cells, yeast, such as *Saccharomyces*, cells, insect cells, such as *Drosophila* or *Spodoptera* cells, and mammalian cells such as HeLa, CHO, 3T3, C127, BHK, COS, etc., cells.

The construction of expression vectors in accordance with the invention, and the transformation of the host cells, can be carried out by means of conventional molecular biology techniques.

Monovalent ligands of the human CD28 receptor in accordance with the invention can in particular be used, in the same way as the monovalent proteins derived from CD28.3 which are described in PCT application WO 02/051871, for obtaining immunosuppressant medicaments, selectively blocking T cell activation phenomena involving the CD28 receptor.

These medicaments can be used in any of the T-lymphocyte-dependent pathological conditions.

These are essentially transplant rejection, graft versus host disease, T-lymphocyte-mediated autoimmune diseases such as type I diabetes, or multiple sclerosis, and type IV hypersensitivity, which is involved in allergic phenomena and also in the pathogenesis of chronic inflammatory diseases following an infection with a pathogenic agent (in particular leprosy, tuberculosis, leishmaniasis, listeriosis, etc.). They may also be diseases such as myeloma, in which lymphocytes experience a dysregulated proliferation, said dysregulated proliferation being dependent on a CD28-transmitted signal (Bahlis et al., Blood., 109 (11):5002-10, 2007).

The present invention will be better understood by means of the further description which follows, which refers to an example illustrating the identification of the epitope recognized by the CD28.3 antibody.

EXAMPLE

Identification of the Epitope Recognized By the Cd28.3 Antibody

In order to determine the epitope recognized by the CD28.3 antibody, Fab fragments of CD28.3 were brought into contact with human CD28 (R&D Systems, Lille, France) immobilized on Sepharose®. The immune complexes were reduced and alkylated by incubation for one hour in the presence of iodoacetamide (55 mM), before the addition of chymotrypsin (1 mg/50 mg of bound antibody), followed by incubation for 4 h at 18-25° C. The Sepharose® was then washed with 25 mM of ammonium carbonate, and then 50 mM glycine, pH 2.5. The peptides eluted were then concentrated on a C18 matrix and analyzed by MALDI-TOF/TOF mass spectrometry, in order to establish the peptide mass fingerprint.

The results of this analysis show that the fragments protected against proteolysis by the chymotrypsin are located in loops C-D-E-F of the CD28 molecules, and therefore constitute a conformational epitope. The sequence of the CD28 receptor region where this epitope is located is represented in FIG. 1, and the sequences of the peptide fragments which form the epitope, and also their locations with respect to the domains of human CD28, are listed in table I below.

TABLE I

| Human CD28 domain | Sequence of the peptide protected against proteolysis |
|---|---|
| C | SREFRASLHKGL (SEQ ID NO: 2) |
| D | NCDGKL (SEQ ID NO: 3) |
| E/F | VTFYLQNLYVNQTDIYFCKIEVM (SEQ ID NO: 4) |

The invention claimed is:

1. In a method for selecting a monovalent ligand of human CD28 receptor which blocks the binding of B7.1 or B7.2 proteins to said CD28 receptor without activating said receptor, comprising the steps of:
   (i) providing candidate monovalent ligands of said CD28 receptor, wherein said ligands are selected from the group consisting of Fv, Fab and scFv fragments of an anti-CD28 antibody, and recombinant proteins comprising said fragments and a heterologous polypeptide,
   (ii) testing said candidate ligands for the ability to block the binding of B7.1 and B7.2 to said CD28 receptor and for the ability to activate said receptor, and
   (iii) selecting the ligands which block the binding of B7.1 or B7.2 to said CD28 receptor without activating said receptor,
   the improvement comprises an additional method step between steps (i) and (ii), wherein the additional step comprises providing a human CD28 receptor or a fragment thereof comprising the conformational epitope formed by the stretches of amino acids of SEQ ID NO:2, SEQ ID NO:3 and SEQ ID NO:4 of said CD28 receptor, testing said candidate ligands for binding to said epitope, and selecting ligands which bind to said epitope.

2. The method of claim 1, wherein the method consists of the steps of:
   (i) providing candidate monovalent ligands of said CD28 receptor, wherein said ligands are selected from the group consisting of Fv, Fab and scFv fragments of an anti-CD28 antibody, and recombinant proteins comprising said fragments and a heterologous polypeptide,
   (ii) testing said candidate ligands for the ability to block the binding of B7.1 and B7.2 to said CD28 receptor and for the ability to activate said receptor, and (iii) selecting the ligands which block the binding of B7.1 or B7.2 to said CD28 receptor without activating said receptor, the improvement comprises an additional method step between steps (i) and (ii), wherein the additional step comprises providing a human CD28 receptor or a fragment thereof comprising the conformational epitope formed by the stretches of amino acids of SEQ ID NO:2, SEQ ID NO:3 and SEQ ID NO:4 of said CD28 receptor, testing said candidate ligands for binding to said epitope, and selecting ligands which bind to said epitope.

\* \* \* \* \*

SEQUENCE LISTING

```
<160> NUMBER OF SEQ ID NOS: 4

<210> SEQ ID NO 1
<211> LENGTH: 134
<212> TYPE: PRT
<213> ORGANISM: Homo sapiens

<400> SEQUENCE: 1

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30
```

-continued

```
Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
        115                 120                 125

Pro Gly Pro Ser Lys Pro
    130

<210> SEQ ID NO 2
<211> LENGTH: 12
<212> TYPE: PRT
<213> ORGANISM: Homo sapiens

<400> SEQUENCE: 2

Ser Arg Glu Phe Arg Ala Ser Leu His Lys Gly Leu
1               5                   10

<210> SEQ ID NO 3
<211> LENGTH: 6
<212> TYPE: PRT
<213> ORGANISM: Homo sapiens

<400> SEQUENCE: 3

Asn Cys Asp Gly Lys Leu
1               5

<210> SEQ ID NO 4
<211> LENGTH: 23
<212> TYPE: PRT
<213> ORGANISM: Homo sapiens

<400> SEQUENCE: 4

Val Thr Phe Tyr Leu Gln Asn Leu Tyr Val Asn Gln Thr Asp Ile Tyr
1               5                   10                  15

Phe Cys Lys Ile Glu Val Met
            20
```